United States Patent
Kohn et al.

[11] Patent Number: 6,120,491
[45] Date of Patent: Sep. 19, 2000

[54] BIODEGRADABLE, ANIONIC POLYMERS DERIVED FROM THE AMINO ACID L-TYROSINE

[75] Inventors: Joachim B. Kohn, Highland Park; Durgadas Bolikal, Edison; George L. Brode, Bridgewater, all of N.J.; Sylvie I. Ertel, Habsheim, France; Shuiyun Guan, Piscataway; John E. Kemnitzer, Plainsboro, both of N.J.

[73] Assignee: The State University Rutgers, New Brunswick, N.J.

[21] Appl. No.: 09/056,050

[22] Filed: Apr. 7, 1998

Related U.S. Application Data

[60] Provisional application No. 60/064,656, Nov. 7, 1997.
[51] Int. Cl.[7] .................................................. A61M 31/00
[52] U.S. Cl. ...................... 604/502; 604/175; 604/891.1; 623/11; 528/176; 528/182
[58] Field of Search ............................ 525/432; 528/182, 528/176, 206; 604/502, 175, 91.1; 623/1, 2, 5, 11, 900

[56] References Cited

U.S. PATENT DOCUMENTS

| | | | |
|---|---|---|---|
| 5,099,060 | 3/1992 | Kohn et al. | 560/40 |
| 5,198,507 | 3/1993 | Kohn et al. | 525/432 |
| 5,216,115 | 6/1993 | Kohn et al. | 528/176 |
| 5,317,077 | 5/1994 | Kohn et al. | 528/182 |
| 5,587,507 | 12/1996 | Kohn et al. | 560/40 |
| 5,658,995 | 8/1997 | Kohn et al. | 525/432 |
| 5,670,602 | 9/1997 | Kohn et al. | 528/176 |

*Primary Examiner*—Wynn Wood Coggins
*Assistant Examiner*—N. Kent Gring
*Attorney, Agent, or Firm*—Synnestvedt & Lechner LLP

[57] ABSTRACT

A polymer with a hydrolytically labile backbone and having the structure:

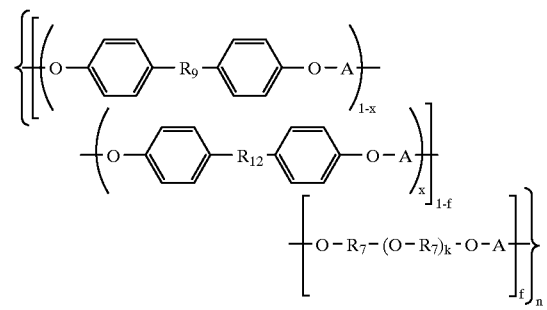

wherein $R_9$ is an alkyl, aryl or alkylaryl group with up to 18 carbon atoms having a pendent carboxylic acid group or the benzyl ester thereof;

$R_{12}$ is an alkyl, aryl or alkylaryl group with up to 18 carbon atoms having a pendent carboxylic acid ester group selected from straight and branched alkyl and alkylaryl esters containing up to 18 carbon atoms and ester derivatives of biologically and pharmaceutically active compounds covalently bonded thereto, provided that the ester group is not a benzyl group or a group that is removed by hydrogenolysis;

each $R_7$ is independently an alkylene group containing up to four carbon atoms;

A is selected from:

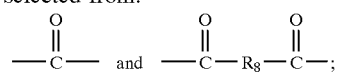

wherein $R_8$ is selected from saturated and unsaturated, substituted and unsubstituted alkyl, aryl and alkylaryl groups containing up to 18 carbon atoms;

k is between about 5 and about 3,000; and x and f independently range from zero to less that one.

50 Claims, 1 Drawing Sheet

BIODEGRADABLE, ANIONIC POLYMERS DERIVED FROM THE AMINO ACID L-TYROSINE

CROSS-REFERENCE TO RELATED APPLICATION

This application claims the benefit of U.S. Provisional patent application Ser. No. 60/064,656 filed on Nov. 7, 1997 by Joachim B. Kohn, Durgadas Bolikal, George L. Brode, Sylvie I. Ertel, Shuiyun Guan and John Kemnitzer entitled, "Biodegradable Anionic Polymers Derived from the Amino Acid L-Tyrosine," now U.S. Pat. No. 5,293,682 the disclosure of which is incorporated herein by reference.

GOVERNMENT LICENSE RIGHTS

The U.S. government has a paid-up license in this invention and the right in limited circumstances to require the patent owner to license others on reasonable terms as required by the terms of Grant Nos. GM-39455 and GM-49849 awarded by the National Institutes of Health.

BACKGROUND OF THE INVENTION

The present invention relates to biodegradable anionic polycarbonates and polyarylates having pendent carboxylic acid groups, and to block copolymers thereof with poly (alkylene oxides). The present invention further relates to species of the above-listed polymers having pendent carboxylic acid ester groups, and, more specifically, to pendent benzyl ester groups and the selective removal of such benzyl esters to form pendent carboxylic acid groups by palladium (Pd)-catalyzed hydrogenolysis of the benzyl esters. The present invention further relates to polycarbonates, polyarylates, and poly(alkylene oxide) block copolymers thereof that are homopolymers and copolymers of tyrosine-derived diphenol monomers having pendent benzyl carboxylate groups.

Diphenols are monomeric starting materials for polycarbonates, polyiminocarbonates, polyarylates, polyurethanes, and the like. Commonly owned U.S. Pat. Nos. 5,099,060 and 5,198,507 disclose amino acid-derived diphenol compounds, useful in the polymerization of polycarbonates and polyiminocarbonates. The resulting polymers are useful as degradable polymers in general, and as tissue-compatible bioerodible materials for medical uses, in particular. The suitability of these polymers for this end use application is the result of their polymerization from diphenols derived from the naturally occurring amino acid, L-tyrosine. The disclosures of U.S. Pat. Nos. 5,099,060 and 5,198,507 are hereby incorporated by reference. These previously-known polymers are strong, water-insoluble materials that can best be used as structural implants.

The same monomeric L-tyrosine derived diphenols were also used in the synthesis of polyarylates as described in commonly owned U.S. Pat. No. 5,216,115, and in the synthesis of poly(alkylene oxide) block copolymers with the aforementioned polycarbonates and polyarylates, which is disclosed in commonly owned U.S. Pat. No. 5,658,995. The disclosures of U.S. Pat. Nos. 5,216,115 and 5,658,995 are also hereby incorporated by reference.

The polycarbonates, polyarylates and poly(alkylene oxide) block copolymers thereof cannot be prepared by conventional solution processes from monomers having free carboxylic acid groups. Therefore, one must selectively incorporate removable protecting groups that can be cleaved after the polymer is formed, without significant degradation of the polymer backbone. The protecting groups are needed to prevent cross-reaction of these otherwise free carboxylic acid groups (i) with the phosgene used in the preparation of polycarbonates and (ii) with the carbodiimide reagents used in the preparation of polyarylates.

The resulting polymers with protected carboxylic acid groups are limited in application because of their slow rate of degradation and significant hydrophobicity. The free acid form of the polymers, in which the ester protecting groups have been removed from the pendent carboxylic acid chains of the diphenols, would be less hydrophobic and thus would be expects to exhibits somewhat increased degradation rates.

In polycarbonates, polyarylates and poly(alkylene oxide) block copolymers thereof prepared from tyrosine-derived diphenol monomers, the backbone contains bonds that are designed to degrade in aqueous media (acidic, neutral, or basic). Thus, the selective removal of any carboxylic acid protecting groups is a challenge. For polyarylates and poly (alkylene oxide) block copolymers thereof, the ester protecting groups cannot be removed by conventional hydrolysis techniques without complete degradation of the polymer backbone. For polycarbonates and poly(alkylene oxide) block copolymers thereof, the ester protecting groups cannot be removed by conventional hydrolysis techniques without massive degradation of the polymer backbone. Since cleavage of the pendent ester groups becomes slower (relative to backbone cleavage) as the bulkiness of the pendent group increases, conventional hydrolysis of methyl and ethyl ester pendent chains is accompanied by a dramatic loss of molecular weight, while attempts to remove bulkier ester pendent chains by either basic or acidic hydrolysis of polycarbonates results in total destruction of the polymer and the recovery of oligomeric species only. Thus, conventional hydrolysis of polycarbonates and poly(alkylene oxide) block copolymers thereof is of marginal value if applied to methyl or ethyl ester pendent chains and is entirely unsuitable for the removal of bulkier pendent chains.

There exist several needs that can be addressed by the incorporation of free carboxylic acid groups to the above mentioned polymer systems. First, the presence of free carboxylic acid groups on polymeric surfaces allows for the modification of the surface properties via the chemical attachment of selected pendent chains, the attachment of biologically active molecules, or the attachment of drugs moieties. Second, the presence of free carboxylic acid groups by itself is a strong regulator of cell attachment, growth and migration on polymeric surfaces. This is of particular importance in the design of medical implant materials that are used in tissue engineering applications where the exact control of cell attachment, spreading and proliferation is a key to the success of the tissue engineering implant.

There exists a need for degradable, biocompatible polymer systems whose design includes the convenient formation of a pendent carboxylic acid group at each monomeric repeat unit without significant backbone degradation. A second need is the need to control the polymer degradation rate through small changes in polymer composition.

SUMMARY OF THE INVENTION

These needs are met by the present invention. It has now been found that the incorporation of pendent carboxylic acid groups within the polymer bulk has a dramatic and previously unrecognized accelerating effect on the rate of polymer backbone degradation and resorption both in vitro and in vivo. Thus, the present invention makes it possible to modulate the rates of degradation and resorption to such a surprising extent that rod-like devices can be formulated that resorb completely form about 5 hours all the way to 3 years post implantation—simply by modifying the percentage of pendent carboxylic-acid pendent chains available along the polymer backbone.

The present invention makes it possible to create pendent carboxylic acid groups on the polymer surface without concomitant backbone cleavage. This is in important difference relative to conventionally used medical polymers such as poly(lactic acid), poly(glycolic acid), polycaprolactone and others where the polymer backbone has to be cleaved (with the associated reduction in molecular weight and physical strength) in order to create chemically reactive attachment sites at the polymer surface. Thus, the present invention significantly improves the versatility and utility of the above mentioned polymer systems, specifically polycarbonates, polyarylates, and the respective poly (alkylene oxide) copolymers thereof.

Thus, a new method has now been discovered for preparing new polymeric materials in which the ester of pendent carboxylic acid groups is selectively removed from the polymer backbone. The resulting polymers contain pendent carboxylic acid groups on some or all of their monomeric repeating subunits. The pendent carboxylic acid groups impart increased hydrophilicity to the polymers and result in unexpected useful new properties. Polycarbonates, polyarylates, and poly(alkylene oxide) block copolymers thereof, with pendent carboxylic acid groups have been prepared.

In particular, it has now been discovered that benzyl esters of pendent polymer carboxylic acid groups may be selectively removed by palladium-catalyzed hydrogenolysis in N,N-dimethylformamide (DMF) or similar solvents such as N,N-dimethylacetamide (DMA) and N-methylpyrrolidone (NMP) to form pendent carboxylic acid groups. Although this reaction is very well known in the literature for the removal of benzyl esters from monomeric or low molecular weight compounds, the present application of this approach to the selective removal of benzyl ester groups from biodegradable polycarbonates and polyarylates is heretofore unknown. By varying the molar ratio of monomeric repeating subunits having pendent benzyl carboxylate groups to the monomeric repeating subunits having other alkyl or alkylaryl carboxylate groups within a polymer, the molar ratio of monomeric repeating subunits having pendent carboxylic acid groups within a polymer may be varied after completion of the selective removal of the benzyl carboxylate groups.

Therefore, according to one aspect of the present invention, polymers are provided having monomeric repeating units defined in Formula I as follows:

Formula I

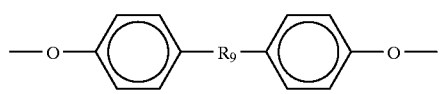

Formula I represents a diphenolic unit wherein $R_9$ is an alkyl, aryl or alkylaryl group with up to 18 carbons with the specific proviso that this group contains as part of its structure a carboxylic acid group or the benzyl ester thereof. $R_9$ can also contain non-carbon atoms such as nitrogen and oxygen. In particular, $R_9$ can have a structure related to derivatives of the natural amino acid tyrosine, cinnamic acid, or 3-(4-hydroxyphenyl)propionic acid. In these cases, $R_9$ assumes the specific structures shown in Formulae II and III.

Formula II

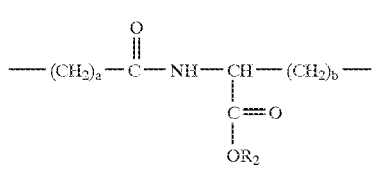

Formula III

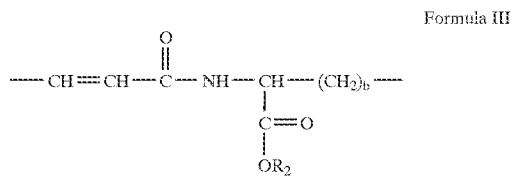

The indicators a and b in Formulae II and III can be independently 0, 1, or 2. $R_2$ is hydrogen or a benzyl group.

A second diphenolic subunit of the polymer is defined in Formula IV. In this second diphenolic subunit, $R_{12}$ is an alkyl, aryl or alkylaryl group substituted with a carboxylic acid ester group, wherein the ester is selected from straight and branched alkyl and alkylaryl esters containing up to 18 carbon atoms, and ester derivatives of biologically and pharmaceutically active compounds covalently bonded to the polymer provided that the ester group is not a benzyl group or any other chemical moiety that may potentially be cleaved by hydrogenolysis. $R_{12}$ can also contain non-carbon atoms such as nitrogen and oxygen. In particular, $R_{12}$ can have a structure related to derivatives of the natural amino acid tyrosine, cinnamic acid, or 3-(4-hydroxyphenyl) propionic acid.

Formula IV

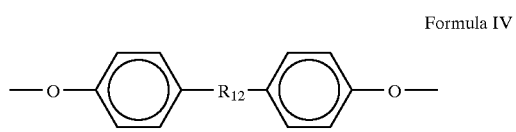

For derivatives of tyrosine, 3-(4-hydroxyphenyl) propionic acid and cinnamic acid, $R_{12}$ assumes the specific structures shown in Formulae V and VI;

Formula V

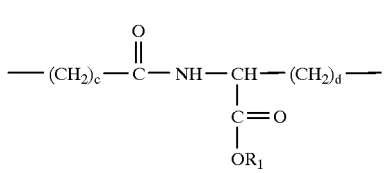

Formula VI

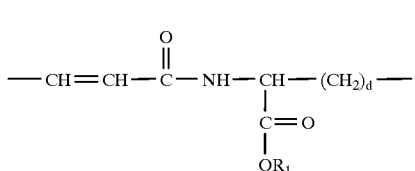

The indicators c and d can be independently 0, 1 or 2. $R_1$ is selected from straight and branched alkyl and alkylaryl groups containing up to 18 carbon atoms, and ester derivatives of biologically active compounds covalently bonded to the diphenol, provided that $R_1$ is not a benzyl group.

Some polymers of this invention may also contain blocks of poly(alkylene oxide) as defined in Formula VII. In Formula VII, $R_7$ is independently an alkylene group containing up to 4 carbons and k is between and 5 and 3,000.

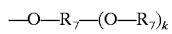

Formula VII

A linking bond, designated as "A" is defined to be either

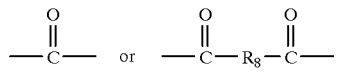

where $R_8$ is selected from saturated and unsaturated, substituted and unsubstituted alkyl, aryl and alkylaryl groups containing up to 18 carbon atoms. Thus, polymers in accordance with the present invention have the structure of Formula VIII:

Formula VIII

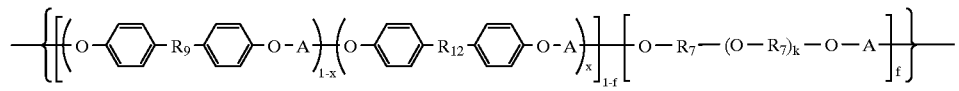

In formula VIII, x and f are the molar ratios of the various subunits. X and f can range from 0 to 0.99. It is understood that the presentation of Formula VIII is schematic and that the polymer structure presented by Formula VIII is a true random copolymer where the different subunits can occur in any random sequence throughout the polymer backbone. Formula VIII provides a general chemical description of polycarbonates when A is

and of polyarylates when A is

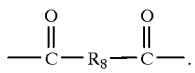

Furthermore, several limiting cases can be discerned: When x=0, the polymer contains only benzyl ester pendent chains which, after hydrogenolysis as described below, will provide pendent carboxylic acid groups at each diphenolic repeat unit. If x is any fraction greater than 0 but smaller than 1, a copolymer is obtained that contains a defined ratio of benzyl ester and non-benzyl ester carrying pendent chains. After hydrogenolysis, a copolymer is obtained that contains a defined ratio of carboxylic acid groups as pendent chains.

If f=0, the polymers do not contain any poly(alkylene oxide) blocks. The frequency at which poly(alkylene oxide) blocks can be found within the polymer backbone increases as the value of f increases.

According to another aspect of the invention, a method is provided for the preparation of the above-defined polymers by:

preparing a reaction mixture of a polymer having the structure of Formula VIII, in which $R_9$ has a pendent benzyl-protected carboxylic acid group, in a anhydrous reaction solvent consisting essentially of one or more solvents selected from DMF, DMA and NMP;

and contacting the reaction mixture with a palladium catalyst in the presence of a hydrogen source so that the benzyl ester groups are selectively removed by hydrogenolysis.

Benzyl group removal by hydrogenolysis in the present invention has been successfully performed upon polycarbonates, polyarylates and poly(alkylene oxide) block copolymers thereof when a benzyl ester protecting group was present. The polymers may be homopolymers of the first repeating subunit of Formula I, or the polymers may be copolymers of the first repeating subunit of Formula I and a second repeating subunit having a structure of Formula IV. The polymers may also contain poly(alkylene oxide) blocks as defined in Formula V and the linking bond "A" may be

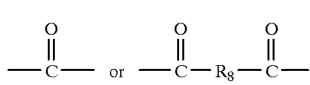

where $R_8$ is selected from saturated and unsaturated, substituted and unsubstituted alkyl, aryl and alkylaryl groups containing up to 18 carbon atoms.

The present invention incorporates the discovery that pure DMF, DMA, or NMP are necessary as the reaction solvent. It was a surprising and unexpected result that no reaction was observable in methylene chloride, methanol, or solvent mixtures containing various ratios of methylene chloride, methanol, and DMF. Another unexpected result was that the reaction medium has to be anhydrous and that the solvents have to be dried to ensure complete removal of all benzyl ester groups in the hydrogenolysis reaction. In preferred methods in accordance with the present invention, the palladium catalyst is palladium on barium sulfate. This catalyst is recoverable and reusable, thereby dramatically reducing the cost of the hydrogenolysis Preferred methods in accordance with the present invention also use 1,4-cyclohexadiene, a transfer hydrogenolysis reagent, in combination with hydrogen gas as a hydrogen source. It has been unexpectedly discovered that at ambient pressure the hydrogenolysis can be accelerated dramatically by the exposure of the reaction mixture to a combination of 1,4-cyclohexadiene and hydrogen gas. If desired, the reaction can be performed at high pressure in a PARR hydrogenolysis apparatus. At high pressure conditions, the addition of 1,4-cyclohexadiene is not required to ensure complete removal of all benzyl ester groups from the polymers.

The benzyl carboxylate polycarbonate homopolymers and copolymers of the present invention are novel and non-obvious intermediate compounds having utility in the preparation of polycarbonates having pendent carboxylic acid groups. Likewise, the benzyl carboxylate polyarylate homopolymers and copolymers of the present invention are novel and non-obvious intermediate compounds having utility in the preparation of polyarylates having pendent carboxylic acid groups.

The polymers of the present invention having pendent carboxylic acid groups meet the need for processible biocompatible biodegradable polymers. Therefore, the present invention also includes implantable medical devices containing the polymers of the present invention having pendent carboxylic acid groups. In one embodiment of the present invention, the polymers are combined with a quantity of a biologically or pharmaceutically active compound sufficient for effective site-specific or systemic drug delivery as described by Gutowska et al., *J. Biomater. Res.*, 29, 811–21 (1995) and Hoffman, *J. Controlled Release*, 6, 297–305 (1987). The biologically or pharmaceutically active compound may be physically admixed, embedded in or dispersed in the polymer matrix. In another embodiment of the present invention, the polymer is in the form of a sheet or a coating applied to exposed injured tissue for use as a barrier for the prevention of surgical adhesions as described by Urry et al., *Mat. Res. Soc. Symp. Proc.*, 292, 253–64 (1993).

Another aspect of the present invention provides a method for site-specific or systemic drug delivery by implanting in the body of a patient in need thereof an implantable drug delivery device containing a therapeutically effective amount of a biologically or pharmaceutically active compound in combination with a polymer of the present invention. Yet another aspect of the present invention provides a method for preventing the formation of adhesions between injured tissues by inserting as a barrier between the injured tissues a sheet or a coating of a polymer of the present invention.

As noted above, derivatives of biologically and pharmaceutically active compounds, including drugs, can be attached to the polymer backbone by covalent bonds linked to the carboxylic acid pendent chain. This provides for the sustained release of the biologically or pharmaceutically active compound by means of hydrolysis of the covalent bond between the drug and the polymer backbone.

In addition, the pendent carboxylic acid groups of the polymers in the present invention provide the polymers with a pH dependent dissolution rate. This further enables the polymers to be used as coatings in gastrointestinal drug release carriers to protect some biologically and pharmaceutically active compounds such as drugs from degrading in the acidic environment of the stomach. The copolymers of the present invention having a relatively high concentration of pendent carboxylic acid groups are stable and water insoluble in acidic environments but dissolve/degrade rapidly when exposed to neutral or basic environments. By contrast, copolymers of low acid to ester ratios are more hydrophobic and will not degrade/resorb rapidly in either basic or acidic environments. Therefore, another aspect of the present invention provides a controlled drug delivery system in which a biologically or pharmaceutically active agent is physically coated with a polymer of the present invention.

The polymers prepared from tyrosine-derived diphenol compounds having pendent carboxylic acid groups are more hydrophilic. Therefore, the polymers of the present invention having carboxylic acid groups will be more readily resorbable under physiological conditions than the previously known polycarbonates and polyarylates. The polymers of the present invention, because they are more hydrophilic, have a higher water uptake, and when the monomeric subunits having carboxylic acid groups predominate, they are more soluble in aqueous media. When the monomeric repeating subunits having pendent carboxylic acid groups do not predominate, the polymers may slowly dissolve in aqueous media with slower degradation. The dissolution/degradation rates are highly pH dependent.

As noted above, the pendent carboxylic acid groups on the polymers of the present invention can function to regulate cell attachment, growth and migration on the polymer surfaces. Therefore, according to yet another aspect of the present invention, a method is provided for regulating cellular attachment, migration and proliferation on a polymeric substrate by contacting living cells, tissues or biological fluids containing living cells with the polymers of the present invention having pendent carboxylic acid groups. The degree of copolymerization, i.e., the ratio of pendent carboxylic acid groups to pendent ester groups, can be attenuated to provide polymers that promote cellular attachment, migration and proliferation, as well as polymers that inhibit attachment, migration and proliferation.

A more complete appreciation of the invention and many other intended advantages can be readily obtained by reference to the following detailed description of the preferred embodiment and claims, which disclose the principles of the invention and the best modes which are presently contemplated for carrying them out.

DETAILED DESCRIPTION OF THE PREFERRED EMBODIMENT

Figure 1:
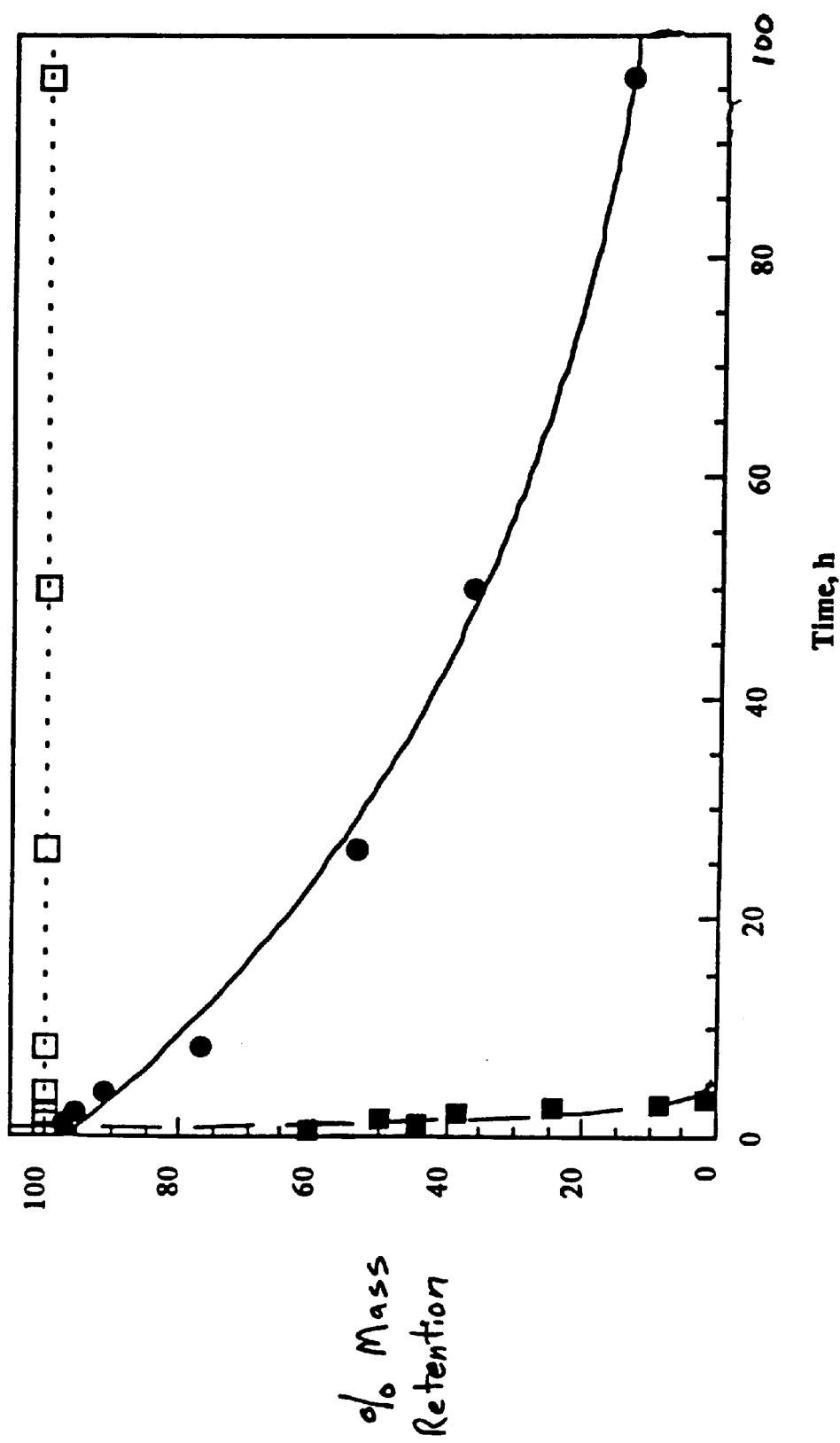
FIG. 1 depicts percent mass retention vs. time of poly (0.5DT-0.5DTE carbonate) (—●—), poly(DT carbonate) (—■—) and poly(DTE carbonate) (—□—) polymer compositions in vitro under physiological conditions.

The method of the present invention provides polycarbonates and polyarylates, as well as poly(alkylene oxide) block polymers thereof, having pendent carboxylic acid groups on some or all of their monomeric subunits. The polymers having pendent carboxylic acid groups are prepared by the hydrogenolysis of polymeric starting materials having corresponding pendent benzyl carboxylate groups. The benzyl carboxylate polymeric starting materials are polymerized from diphenol compounds having benzyl ester-protected pendent carboxylic acid groups, alone, or in combination with diphenol compounds having other ester-protected carboxylic acid groups. In particular, the benzyl carboxylate diphenols have the structure of Formula Ia:

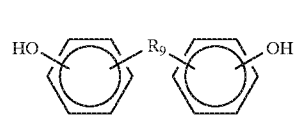

(Ia)

wherein $R_9$ is the same as described above with respect to Formula I, but limited to the species that contains as part of its structure a benzyl ester protected carboxylic acid group. The benzyl carboxylate diphenols preferably have the structure of Formula Ia in which $R_9$ has the structure of Formula II or Formula III in which $R_2$ is a benzyl group. Among the preferred diphenols are compounds in which $R_9$ has the structure of Formula II in which a and b are independently one or two. Most preferably, a is two and b is one. These most preferred compounds are tyrosine dipeptide analogues known as desaminotyrosyl-tyrosine alkyl or alkylaryl esters.

In this preferred group the diphenols can be regarded as derivatives of tyrosyl-tyrosine dipeptides from which the N-terminal amino group has been removed.

Diphenol compounds having other ester-protected carboxylic acid groups have the structure of Formula IVa:

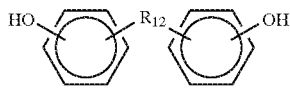

(IVa)

wherein $R_{12}$ is the same as described above with respect to Formula IV. $R_{12}$ preferably has the structure of Formula V or Formula VI. More preferably, $R_{12}$ has the structure of Formula V in which c and d are preferably independently one or two. Most preferably, c is two and d is one.

Methods for preparing the diphenol monomers are disclosed in commonly owned U.S. Pat. Nos. 5,587,507 and 5,670,602, the disclosures of both of which are hereby incorporated by reference. The preferred desaminotyrosyl-tyrosine esters are the ethyl, butyl, hexyl, octyl and benzyl esters. For purposes of the present invention, desaminotyrosyl-tyrosine ethyl ester is referred to as DTE, desaminotyrosyl-tyrosyl-tyrosine benzyl ester is referred to as DTBn, and the like. For purposes of the present invention, the desaminotyrosyl-tyrosine free acid is referred to as DT.

The polymers of the present invention may be homopolymers with each monomeric subunit having a pendent carboxylic acid group prepared by the hydrogenolysis of corresponding benzyl carboxylate homopolymers. Copolymers of diphenol monomers having pendent carboxylic acid ester groups, and diphenol monomers having pendent carboxylic acid groups can also be incorporated into the basic backbone structure of the polymers by the hydrogenolysis of corresponding copolymers of benzyl ester monomers and monomers having pendent esters other than benzyl carboxylates.

Thus, for example, poly(DT carbonates) are prepared by the hydrogenolysis of poly(DTBn carbonates), poly(DT-DTE carbonate) copolymers are prepared by the hydrogenolysis of poly(DTBn-DTE carbonate) copolymers, and so forth. One can thus vary within polymers the molar ratios of the monomeric subunits having pendent alkyl and alkylaryl ester groups and the monomeric subunits having pendent carboxylic acid groups.

Polymers in accordance with the present invention include homopolymers of a repeating unit having a pendent carboxylic acid group. Such homopolymers have the structure of Formula VIII in which x and f are both zero and $R_9$ is the same as described above with respect to Formula I with the proviso that it is limited to species having pendent carboxylic acid groups The homopolymers are prepared by the hydrogenolysis of corresponding homopolymers having the structure of Formula VIII in which x and f are both zero and $R_9$ is the same as described above with respect to Formula I, with the proviso that it is limited to species having pendent benzyl carboxylate groups.

Polymers in accordance with the present invention also include copolymers having pendent carboxylic acid groups with the structure of Formula VIII in which f is zero, x is a number greater than zero but less than one, $R_{12}$ is the same as described above with respect to Formula IV and $R_9$ is the same as described above with respect to Formula I, with the proviso that it is limited to species with pendent carboxylic acid groups. In copolymers in accordance with the present invention, x is preferably between about 0.50 and about 0.90 and more preferably between about 0.60 and about 0.80.

Copolymers having pendent carboxylic acid groups are prepared by the hydrogenolysis of corresponding copolymers having the structure of Formula VIII in which f is zero, x is a number greater than zero but less than one, $R_{12}$ is the same as described above with respect to Formula IV and $R_9$ is the same as described above with respect to Formula I, with the proviso that it is limited to species with pendent benzyl carboxylate groups. In preferred copolymers in accordance with the present invention, $R_9$ has the structure of either Formula II or Formula III and $R_{12}$ has the structure of either Formula V or Formula VI, in which $R_1$, $R_2$, a, b, c and d are the same as described above with respect to Formulae II, III, V and VI.

In more preferred copolymers, $R_9$ has the structure of Formula II and $R_{12}$ has the structure of Formula V in which a, b, c and d are independently one or two. Most preferably, a and c are two and b and d are one.

When A of Formula VIII is:

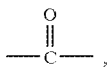

the polymers of the present invention are polycarbonates. The polycarbonate homopolymer and copolymer starting materials having pendent benzyl carboxylate groups may be prepared by the method described by U.S. Pat. No. 5,099,060 and by U.S. patent application Ser. No. 08/884,108 filed Jun. 27, 1997, the disclosures of both of which are also incorporated herein by reference. The described method is essentially the conventional method for polymerizing diphenols into polycarbonates. Suitable processes, associated catalysts and solvents are known in the art and are taught in Schnell, *Chemistry and Physics of Polycarbonates*, (Interscience, New York 1964), the teachings of which are incorporated herein by reference.

Polycarbonate homopolymers and copolymers in accordance with the present invention having pendent carboxylic acid groups, and the polycarbonates having pendent benzyl carboxylate groups from which they are prepared, have weight-average molecular weights ranging between about 20,000 to about 400,000 daltons, and preferably about 100,000 daltons, measured by gel permeation chromatography (GPC) relative to polystyrene standards without further correction.

When A of Formula VIII is:

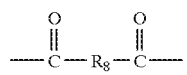

the polymers of the present invention are polyarylates. The polyarylate homopolymer and copolymer starting materials having pendent benzyl carboxylate groups may be prepared by the method described by U.S. Pat. No. 5,216,115, in which diphenol compounds are reacted with aliphatic or aromatic dicarboxylic acids in a carbodiimide mediated direct polyesterification using 4-(dimethylamino) pyridinium-p-toluene sulfonate (DPTS) as a catalyst to form aliphatic or aromatic polyarylates. The disclosure of this patent is also incorporated herein by reference. It should be noted that $R_8$ should not be substituted with functional groups that would cross-react with the dicarboxylic acids.

Dicarboxylic acids from which the polyarylate starting materials of the present invention may be polymerized have the structure of Formula IX:

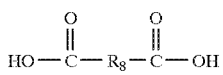

$$HO-\overset{O}{\overset{\|}{C}}-R_8-\overset{O}{\overset{\|}{C}}-OH \qquad (IX)$$

in which, for the aliphatic polyarylates, $R_8$ is selected from saturated and unsaturated, substituted and unsubstituted alkyl groups containing up to 18 carbon atoms, and preferably from 4 to 12 carbon atoms. For aromatic polyarylates, $R_8$ is selected from aryl and alkylaryl groups containing up to 18 carbon atoms, but preferably from 8 to 14 carbon atoms. Again, $R_8$ should not be substituted with functional groups that would cross-react with the diphenols.

$R_8$ is even more preferably selected so that the dicarboxylic acids from which the polyarylate starting materials are polymerized are either important naturally-occurring metabolites or highly biocompatible compounds. Preferred aliphatic dicarboxylic acids therefore include the intermediate dicarboxylic acids of the cellular respiration pathway known as the Krebs Cycle. These dicarboxylic acids include alpha-ketoglutaric acid, succinic acid, fumaric acid, maleic acid and oxalacetic acid. Other preferred biocompatible aliphatic dicarboxylic acids include sebacic acid, adipic acid, oxalic acid, malonic acid, glutaric acid, pimelic acid, suberic acid and azelaic acid. Among the preferred aromatic dicarboxylic acids are terephthalic acid, isophthalic acid and bis(p-carboxyphenoxy) alkanes such as bis(p-carboxylphenoxy) propane. Stated another way, $R_8$ is more preferably a moiety selected from $-CH_2-C(=O)-$, $-CH_2-CH_2-C(=))-$, $CH=CH-$ and $(-CH_2-)_z$, wherein z is an integer between two and eight inclusive.

Polyarylate homopolymers and copolymers in accordance with the present invention having pendent carboxylic acid groups, and the corresponding polyarylates having pendent benzyl carboxylate groups from which they are prepared, have weight average molecular weights between about 20,000 and about 40,000 daltons, and preferably about 100,000 daltons, measured by GPC relative to polystyrene standards without further correction.

Polycarbonates and polyarylates in accordance with the present invention also include random block copolymers with a poly(alkylene oxide) having pendent carboxylic acid groups with the structure of Formula VIII, wherein f is greater than zero but less than one, $R_{12}$ is the same as described above with respect to Formula IV, k and $R_7$ are the same as described above with respect to Formula VII and $R_9$ is the same as described above with respect to Formula I, with the proviso that it is limited to species having pendent carboxylic acid groups. The value for x is less than one, but x may or may not be greater than zero.

The molar fraction of alkylene oxide in the block copolymer, f, ranges between about 0.01 and about 0.99. The block copolymers having pendent carboxylic acid groups are prepared by the hydrogenolysis of corresponding block copolymers having the structure of Formula VIII, wherein x is greater than zero but less than one, $R_{12}$ is the same as described above with respect to Formula IV, k and $R_7$ are the same as described above with respect to Formula VII, and $R_9$ is the same as described above with respect to Formula I, with the proviso that it is limited to species having pendent benzyl carboxylate groups. Again, the value for x is less than one, but may or may not be greater than zero.

For preferred polymeric starting materials and the resulting free acid block copolymers, $R_7$ is ethylene, k is between about 20 and about 200, and the molar fraction of alkylene oxide in the block copolymer, f, preferably ranges between about 0.05 and about 0.75. $R_7$ may also represent two or more different alkylene groups within a polymer.

The block copolymers of the present invention having pendent benzyl carboxylate groups may be prepared by the method described by U.S. Pat. No. 5,658,995, the disclosure of which is also incorporated herein by reference. For block copolymers of the present invention having either pendent carboxylic acid groups or pendent benzyl carboxylate groups in which x is greater than zero, the molar fraction of alkylene oxide and block copolymer, f, will remain between about 0.01 and about 0.99.

The block copolymers in accordance with the present invention having pendent carboxylic acid groups, and the block copolymers having pendent benzyl carboxylate groups from which they are prepared, have weight-average molecular weights between about 20,000 and about 400,000 daltons, and preferably about 100,000 daltons. The number-average molecular weights of the block copolymers are preferably above about 50,000 daltons. Molecular weight determinations are measured by GPC relative to polystyrene standards without further correction.

For the copolymers of the present invention having the structure of Formula VIII in which x is greater than zero, the pendent carboxylic acid ester group of $R_{12}$ can be an ester derivative of a biologically or pharmaceutically active compound covalently bonded to the polycarbonate or polyarylate copolymer. The covalent bond is by means of an amide bond when in the underivatized biologically or pharmaceutically active compound a primary or secondary amine is present at the position of the amide bond in the derivative. The covalent bond is by means of an ester bond when in the underivatized biologically or pharmaceutically active compound a primary hydroxyl is present at the position of the ester bond in the derivative. The biologically or pharmaceutically active compounds may also be derivatized at a ketone, aldehyde or carboxylic acid group with a linkage moiety that is covalently bonded to the copolymer or diphenol by means of an amide or ester bond.

Detailed chemical procedures for the attachment of various drugs and ligands to polymer bound free carboxylic acid groups have been described in the literature. See, for example, Nathan et al., *Bio. Cong. Chem.*, 4, 54–62 (1993). The disclosure of this publication is incorporated herein by reference.

Examples of biologically or pharmaceutically active compounds suitable for use with the present invention include acyclovir, cephradine, malphalen, procaine, ephedrine, adriamycin, daunomycin, plumbagin, atropine, quinine, digoxin, quinidine, biologically active peptides, chlorin $e_6$, cephradine, cephalothin, cis-hydroxy-L-proline, melphalan, penicillin V, aspirin, nicotinic acid, chemodeoxycholic acid, chlorambucil, and the like. The compounds are covalently bonded to the polycarbonate or polyvarylate copolymer by methods well under stood by those of ordinary skill in the art. Drug delivery compounds may also be formed by physically blending the biologically or pharmaceutically active compound to be delivered with the polymers of the present invention having pendent carboxylic acid groups using conventional techniques well-known to those of ordinary skill in the art.

For purposes of the present invention biologically active compounds are also defined as including crosslinking moieties, such as molecules with double bonds (e.g., acrylic acid derivatives), which can be attached to the pendent carboxylic acid groups for crosslinking to increase the strength of the polymers. Biologically active compounds, for purposes of the present invention, are additionally defined as including cell attachment mediators, biologically active ligands and the like.

As noted above, the polymers of the present invention contain pendent carboxylic acid groups at selected repeating subunits. For the purposes of the present invention, homopolymers (Formula VIII, x=0) are defined as containing a pendent carboxylic acid group at each diphenolic subunit. These homopolymers can be polycarbonates or polyarylates and may contain polyalkylene oxide blocks. The homopolymers are best described as new, degradable polyanions that may have a number of pharmacological and biological activities. Likewise, for the purpose of the present invention, copolymers (Formula VIII, 0<x<1) are defined as containing a pendent carboxylic acid group at some of the diphenolic subunits. These copolymers can be polycarbonates or polyarylates and may contain polyalkylene oxide blocks.

In terms of processibility, homopolymers (as defined above) tend to have very high glass transition temperatures because of strong intrachain and interchain hydrogen bonding. Homopolymers are soluble in water because of the high density of free carboxylic acid groups present and have a pH-dependent solubility profile. Their solubility is significantly reduced in slightly acidic media. Homopolymers are also soluble in commonly used organic solvents such as mixtures of methylene chloride and methanol. Because of their solubility in both water and organic media, they can be processed by solvent casting techniques and are good film formers. Homopolymers can also be processed into porous foams by salt leaching techniques as described in Freed et al., *J. Biomed. Mater. Res.*, 27, 11–23 (1993), as long as the aqueous extraction steps are performed in slightly acidic media (pH 4–5) so that the homopolymers do not dissolve. Homopolymers can also be processed into porous foams by phase separation techniques, as described in Schugens et al., *J. Biomed. Meter. Res.*, 30, 449–462 (1995) as long as a saturated solution of sodium chloride is used instead of water as the "non-solvent". The disclosure of these publications is incorporated herein by reference.

The copolymers as defined above may contain from about 1 to about 99 mole percent of monomeric subunits having pendent carboxylic acid groups. Their properties are strongly affected by the mole fraction of free carboxylic acid groups present. Copolymers that have less than 20 molar percent of monomeric repeating subunits with pendent carboxylic acid groups are processible by compression molding and extrusion. As a general rule, copolymers with less than 20 molar percent of monomeric repeating subunits with pendent carboxylic acid groups are not soluble in water.

For copolymers having more than 20 mole percent of monomeric subunits with pendent carboxylic acid groups, some thermal degradation has been observed during conventional compression molding and extrusion at elevated temperatures. Copolymers having more than 20 mole percent of monomeric subunits with pendent carboxylic acid groups tend to exhibit increased swelling (due to imbibition of water) during exposure to aqueous media and when more than about 50 mole percent of monomeric subunits carry free carboxylic acid groups, the copolymer tend to become water soluble and their behavior will be similar to the behavior of the corresponding homopolymers, which dissolve in pH 7.4 phosphate buffer to the extent of about 2 mg/mL.

Irrespective of the amount of carboxylic acid groups, all copolymers of the present invention are good film-forming materials. Copolymers having less than about 70 mole percent of monomeric subunits with pendent carboxylic acid groups can be processed into porous foams by salt leaching techniques as described in Freed et al., *J. Biomed. Mater. Res.*, 27, 11–23 (1993), or by phase separation techniques, as described in Schugens et al., *J. Biomed. Meter. Res.*, 30, 449–462 (1996). The disclosure of these publications is incorporated herein by reference. Copolymers having more than about 70 mole percent of monomeric subunits with pendent carboxylic acid groups tend to be water soluble and must be processed into porous foams as described for the corresponding homopolymers.

It has now been found that the free carboxylic acid groups have a profound effect on the degradation and resorption rates of the polymers of the present invention. This makes it possible to fine-tune the degradation/resorption of the polymers of the present invention by controlling the molar fraction of free carboxylic acid groups (as defined with respect to Formula VIII). This is a significant advantage over the polycarbonates and polyarylates of the prior art which do not have pendent free carboxylic acid groups and whose degradation/resorption rate could not be readily varied by small changes in the polymer structure. The effect of the free carboxylic acid groups on degradation/resorption can be very dramatic as shown by the example of a polycarbonate: Poly(DTE carbonate) is a polymer defined by Formula VIII where x=1, f=0, and $R_{12}$ is defined by Formula V where c=2, d=1 and $R_1=CH_2-CH_3$. It has been found previously, that this polymer will not lose any mass when stored in phosphate buffered solution under physiological conditions for over 18 months. However, it about 20 mole percent of the $R_1$ groups are replaced by free carboxylic acid groups, thin films of the corresponding copolymer will exhibit significant mass loss after as little as 20 weeks under identical storage conditions. If about 50 percent of the $R_1$ groups are replaced by free carboxylic acid groups, thin films of the corresponding copolymer will completely degrade/dissolve within about one week.

The composition of the polymers of the present invention can also be used to influence the interactions with cells. When the polycarbonates or polyarylates of the present invention do not contain polyalkylene oxide (f=0 in Formula VIII), they can be more adhesive growth substrates for cell cultures compared to the ester-protected polymers of the prior art. The negative charge from the free carboxylic acid groups present on the surface of the polymers has been discovered to improve the attachment and growth of rat lung fibroblasts and may facilitate specific interactions with proteins, peptides and cells. The polymers are thus useful as scaffolding implants for tissue reconstruction. The polymer surfaces may also be modified by simple chemical protocols to attach specific peptides, in particular, the important peptides containing variations of the "RGD" integrin binding sequence known to affect cellular attachment in a profound way. Thus, the ability to immobilize peptides and proteins via the free carboxylic acid groups onto the polymer surface to elicit selective cellular responses will be of major importance in tissue engineering applications and in implant design. The necessary chemical techniques to attach ligands to polymer-bound carboxylic acid groups are well known in the art and have, among others, been described by Nathan et al., *Biconj. Chem.*, 4, 54–62 (1993). The disclosure of this publication is incorporated herein by reference.

On the other hand, the incorporation of polyalkylene oxide blocks decreases the adhesiveness of the polymeric surfaces. Polymers for which f is greater than 5 mole percent according to Formula VIII are resistant to cell attachment and may be useful as non-thrombogenic coatings on surfaces in contact with blood. These polymers also resist bacterial adhesion.

The polymers of the present invention having pendent carboxylic acid groups may be prepared by the palladium-catalyzed hydrogenolysis of corresponding polymers having pendent benzyl carboxylate groups. Essentially any palladium-based hydrogenolysis catalyst is suitable for use with the present invention. Palladium on barium sulfate is preferred because it has been found to be the easiest to separate from the polymer. This not only provides a polymer of high purity, it also permits the efficient recycling of this expensive catalyst.

A level of palladium on barium sulfate between about 5 and about 10 percent by weight is preferred. Lower levels either extend reaction time or reduce yield and higher levels represent an unnecessary expense.

The use of dimethylformamide as the reaction solvent is critical. The polymer starting material having pendent benzyl carboxylate groups should be dissolved in dimethylformamide at a solution concentration (w/v %) between about 5 and about 50 percent, and preferably between about 10 and about 20 percent.

The polymer is stirred until a clear solution is obtained. The palladium catalyst is then added, after which the hydrogen source is supplied to the reaction mixture.

The amount of palladium catalyst to be employed is that amount that is effective to catalyze the hydrogenolysis reaction. The absolute mass ratio of elemental palladium to the polymer is not as important as the surface activity of the elemental palladium. The amount of a catalyst preparation to be used will depend upon the specific catalytic activity of the preparation, and this can be readily determined by one of ordinary skill in the art without undue experimentation.

For a preparation containing about 5 percent by weight of palladium on barium sulfate, between about 15 and about 30 weight percent, and preferably about 25 weight percent, of the preparation should be used relative to the polymeric starting material. If the catalyst preparation is being recycled, higher levels of the preparation will be needed, because as the catalyst is reused, the palladium is slowly deactivated, and the amount used must be adjusted to maintain the stated catalytic activity. However, the increases in catalyst levels needed to adjust for the loss of catalytic activity can also be determined by one of ordinary skill in the art without undue experimentation.

Essentially any hydrogen source for palladium-catalyzed hydrogenolysis is suitable for use with the present invention. For example, the reaction mixture may be supplied with a hydrogen gas blanket. Alternatively, a transfer hydrogenolysis reagent, such as 1,4-cyclohexadiene may be used. The used of a transfer hydrogenolysis reagent in combination with hydrogen gas blanketing is preferred. The reaction rate was found to accelerate dramatically when the two hydrogen sources were used together.

When the transfer hydrogenolysis reagent is employed as a hydrogen source, a stiochiometric excess relative to the polymeric starting material should be employed. With 1,4-cyclohexadiene, this represents an excess up to about 50 weight percent, and preferably about a 10 weight percent excess, relative to the polymeric starting material.

The hydrogenolysis reaction can also be performed under pressure of hydrogen gas in a PARR hydrogenolysis apparatus. Under these conditions, the removal of benzyl ester pendent chains is particularly fast and no transfer hydrogenolysis agent needs to be added. Irrespective of the exact mode of conducting the reaction, it is important to maintain strictly anhydrous conditions.

The progress of the reaction can be measured by monitoring the removal of the benzyl ester from the polymeric starting material in reaction aliquots by NMR spectorscopy. When the reaction has come to completion (about 24 to 48 hours), the polymer is isolated by filtering off the solid palladium catalyst and the filtrate is added into water to precipitate the polymer. The polymer can then be purified by dissolving in 9:1 methylene chloride-methanol (about 10 percent to about 20 percent w/w) and reprecipitating in ether. The polymeric product may then be dried to constant weight under high vacuum.

The polymers of the present invention having pendent carboxylic acid groups are not limited to those polymers prepared by hydrogenolysis. Any other method that allows for the selective removal of a pendent carboxylate ester group is suitable for use in the preparation of the polymers of the present invention. For example, iodotrimethylsilane may be used to selectively remove methyl ester pendent chains in the presence of ethyl ester pendent chains. However, the hydrogenolysis method of the present invention is preferred because it produces a higher reaction yield.

The polymers of the present invention can find application in areas where both solid materials and solvent-soluble materials are commonly employed. Such application include polymeric scaffolds in tissue engineering applications and medical implant applications, including the use of the polycarbonates and polyarylates of the present invention to form shaped articles such as vascular grafts and stents, bone plates, sutures, implantable sensors, barriers for surgical adhesion prevention, implantable drug delivery devices, scaffolds for tissue regeneration, and other therapeutic agent articles that decompose harmlessly within a known period of time.

Controlled drug delivery systems may be prepared, in which a biologically or pharmaceutically active agent is physically embedded or dispersed within a polymeric matrix or physically admixed with a polycarbonate or polyarylate of the present invention. Because the polymers of the present invention have a pH dependent dissolution rate, they are useful as drug coatings for gastrointestinal release to protect some drugs from degrading in the acidic environment of the stomach because the polymers are stable and non-water soluble in acidic environments but dissolve and degrade rapidly when exposed to neutral or basic environments.

The following non-limiting examples set forth hereinbelow illustrate certain aspects of the invention. All parts and percentages are by mole percent unless otherwise noted and all temperatures are in degrees Celsius. Poly(DTBn-DTE carbonates) were prepared using the method disclosed by U.S. Pat. No. 5,099,060. The 5 percent palladium on barium sulfate catalyst, 1,4-cyclohexadiene, and thionyl chloride were obtained from Acros Organics, a division of Fisher Scientific Company. Poly(ethylene glycol) 2000 (PEG 2000) was obtained from Aldrich Chemical Company. Tyrosine benzyl ester as its p-toluenesulfonic acid salt was obtained from Sigma Chemical Company. All solvents were HPLC grade. All other reagents were of analytical grade and were used as received.

EXAMPLES

Examples use the following product characterization procedures.
Spectroscopy
$^1$H NMR spectra and $^{13}$C NMR spectra were recorded respectively at 199.98 MHz and 49.99 MHz on a Varian Gemini 200 in 5 mm tubes at 10 percent (w/v) in deuterated solvents. Chemical shifts are reported in ppm.
Molecular Weights
Molecular weights were determined by GPC on a chromatographic system consisting of a Perkin-Elmer Model 410 pump, a Waters Model 410 Refractive Index Detector and a Perkin-Elmer Model 2600 computerized data station. Two PL-gel GPC columns ($10^5$ and $10^3$ Angstrom pore size, 30 cm length) were operated in series at a flow rate of 1 mL/min tetrahydrofuran (THF). Polymer solutions (5mg/mL) were prepared, filtered (0.45 micron membrane filer) and allowed to equilibrate for 30 minutes prior to injection. The injection volume was 25 microliters. Molecular weights were calculated relative to polystyrene standards (Polymer Laboratories, Inc.) without further corrections.

Thermal Analysis

Determination of product purity was based on melting point depression measured with a TA Instruments 910 Differential Scanning Calorimeter (DSC) calibrated with indium. For determination of the melting temperature, a 2.0 mg sample was subjected to a single run at a heating rate of 1° C./min. over a 60° C. range.

Atomic Absorption

Residual levels of the catalyst preparation were measured by atomic absorption by Quantitative Technologies Inc.

The following table defines the abbreviations adopted for the diphenols illustrated by the example below:

| | |
|---|---|
| Desaminotyrosyl tyrosine free acid | DT |
| Desaminotyrosyl tyrosine ethyl ester | DTE |
| Desaminotyrosyl tyrosine benzyl ester | DTBn |

Example 1

Hydrogenolysis of Poly(DTBn$_{50}$-DTE$_{50}$ Carbonate)

Preparation

In a 500 mL round-bottomed flask was placed 15 g of poly(DTBn-DTE carbonate) which contained DTBn and DTE in a 1:1 ratio. To the flask was then added 150 mL of dry DMF and the mixture was stirred until a clear solution was obtained. To this solution were added 3.5 g of 5 percent Pd on BaSO$_4$ catalyst and 7 mL of 1,4-cyclohexadiene (hydrogen donor). The mixture was stirred at room temperature. A rubber balloon filled with hydrogen gas was attached to the mouth of the flask using a gas inlet adapted. The balloon was replenished with hydrogen as needed. After about 40 h of stirring a 0.5 mL sample was withdrawn, centrifuged, and then precipitated by adding to water with stirring. The precipitate was dried and analyzed by $^1$H NMR, which showed complete conversion of the benzyl groups to free acid. The reaction was stopped and the reaction mixture was centrifuged. The supernatant was filtered using 0.45 $\mu$M syringe filter in several portions. (A celite bed on a fritted glass funnel can also be used for the filtration.) A clear light yellow filtrate was obtained. The filtrate was added to 1.5 L of deionized water with agitation using a mechanical stirrer. (A high speed blender can also be used for the precipitation to obtain finely divided particles.) The precipitated product was isolated by filtration and washed with 750 mL of water in a high speed blender. The product was dried in a nitrogen stream for 16 h and then dried in a vacuum over at room temperature for two days. For further purification, the product was dissolved in 150 mL of 9:1 methylene chloride-methanol and precipitated with 1.5 L of ether and then dried as above.

The hydrogenation can also be carried out in a PARR hydrogenator at high hydrogen pressures (60 psi). When a hydrogenator is used at high hydrogen pressures, the transfer hydrogen donor, 1,4-cyclohexadiene is not necessary.

Structure Proof $^1$H NMR spectrum of the product in DMSO-d$_6$ showed the following resonances ($\delta$, ppm relative to TMS): 8.40 (br s, 1H NH of DTE), 8.25 (br s, 1H NM of DT), 7.15–7.35 (m, 8H, aromatic H's), 4.50 (m, 1H, CH of tyrosine), 4.03 (q, 1H, CH$_2$–CH$_3$), 2.20–3.20 (m, 6H, CH$_2$'s of DAT and Tyrosine), 11.1 (t, 1.5H, CH$_2$–CH$_3$). Also a multiplet that is found in poly(DTBn-DTE carbonate) at 5.1 ppm for benzyl H's was completely absent indicating complete removal of the benzyl protecting group. The equal intensity of the two NH peaks indicate that the DT and DTE are in equal concentration. The ratio of H's of tyrosine CH to the H's of CH$_2$–CH$_3$ show that there is one ethyl ester group for every two monomer subunits. These spectral data indicate that the polymer contains DT and DTE in 1:1 ratio and the benzyl protecting group is completely removed.

Characterization

The molecular weight of the product was determined by GPC using THF as the mobile phase. A M$_w$ of 74 Kda and M$_n$ 47 Kda were obtained. The T$_g$ of the polymer was found to be 114° C. by DSC and the decomposition temperature (for 10 percent decomposition) was 309° C. Atomic absorption measurements showed a Pd concentration of 39 ppm and a barium concentration less than the detection limit (10 ppm).

Example 2

Hydrogenolysis of Poly(DTBn$_{0.05}$-DTE$_{0.95}$ Carbonate)

Preparation

The hydrogenolysis of a 15 gram sample of poly(DTBn-DTE carbonate), which contained DTBn and DTE in a 1:19 ratio and had a M$_w$ of 286 Kda and M$_n$ of 116 Kda was performed as in Example 1.

Structure Proof

The $^1$H NMR spectrum of the product in DMSO-d$_6$ showed the following resonances ($\delta$, ppm relative to TMS): 8.40 (br s, 0.95H, NH of DTE), 8.25 (br s, 0.05H, NH of DT), 7.15–7.35 (m, 8H, aromatic H's), 4.71 (m, 1H, CH of tyrosine), 4.03 (q, 1.9H, CH$_2$–CH$_3$), 2.1–3.3 (m, 6H, CH$_2$'s of DAT and Tyrosine), 1.11 (t, 2.85H, CH$_2$–CH$_3$). Also a multiplet that is found in poly(DTBn-DTE carbonate) at 5.1 ppm due to benzyl H's was completely absent indicating complete removal of the benzyl protecting groups. The 1:19 ratio of the DT-NH peak to the DTE-NH peak indicates that the polymer is made of 5% DT and 95% DTE. The ratio of CH group to the ethyl ester group shows that there are nineteen ethyl ester groups for every twenty monomer subunits. These spectral data indicate that the polymer contains DT and DTE in 0:19 ratio and the benzyl protecting group is completely removed.

Characterization

The molecular weight of the product was determined by GPC using THF as the mobile phase. A M$_w$ of 125 Kda and M$_n$ 55 Kda were obtained. The T$_g$ of the polymer was found to be 96° C. by DSC and the decomposition temperature (for 10% decomposition) was 334° C.

Example 3

Hydrogenolysis of Poly(DTBn$_{0.10}$-DTE$_{0.09}$ Carbonate)

Preparation

Hydrogenolysis of a 15 g sample of poly(DTBn-DTE carbonate) which contained DTBn and DTE in a 1:9 ratio and had a M$_w$ of 183 Kda and M$_n$ of 84 Kda was performed as in Example 1.

Structure Proof

The $^1$H NMR spectrum of the product in DMSO-d$_6$ showed the following resonances ($\delta$, ppm relative to TMS):

8.40 (br s, 0.9H, NH of DTE), 8.25 (br, s, 0.1H, NH of DT), 7.15–7.35 (m, 8H, aromatic H's), 4.50 (m, 1H, CH of tyrosine), 4.03 (q, 1.8H, $CH_2$–$CH_3$), 2.1–3.3 (m, 6H, $CH_2$'s of DAT and Tyrosine), 1.11 (t, 2.7H, $CH_1$–$CH_3$). Also a multiplet that is found in poly(DTBn-DTE carbonate) at 5.1 ppm due to benzyl H's was completely absent indicating complete removal of the benzyl protecting groups. The 1:9 ratio of the DT-NH peak to the DTE-NH peak ester group shows that there are nine ethyl ester groups for every ten monomer subunits. These spectral data indicate that the polymer contains DT and DTE in 1:9 ratio and the benzyl protecting group is completely removed.

Characterization

The molecular weight of the product was determined by GPC using THF as the mobile phase. A $M_w$ of 100 Kda and $M_n$ 46 Kda were obtained. The $T_g$ of the polymer was found to be 98° C. by DSC and the decomposition temperature (for 10% decomposition) was 330° C.

Example 4

Hydrogenolysis of Poly($DTBn_{0.25}$-$DTE_{0.75}$ Carbonate)

Preparation

Hydrogenolysis of a 15 g sample of poly(DTBn-DTE carbonate) which contained DTBn and DTE in a 1:3 ratio and had a $M_w$ of 197 Kda and $M_n$ of 90 Kda was performed as in Example 1.

Structure Proof

The $^1H$ NMR spectrum of the product in DMSO-$d_6$ showed the following resonances (δ, ppm relative to TMS): 8.40(br s, 0.75H, NH of DTE), 8.25 (br s, 0.25H, NH of DT), 7.15–7.35 (m, 8H, aromatic H's), 4.50 (m, 1H, CH of tyrosine), 4.03 (q, 1.5H, $CH_2$–$CH_3$), 2.1–3.3 (m, 6H, $CH_2$'s of DAT and Tyrosine), 1.11 (t, 2.25H, $CH_2$–$CH_3$). Also a multiplet that is found in poly(DTBn-DTE carbonate) at 5.1 ppm due to benzyl H's was completely absent indicating complete removal of the benzyl protecting groups. The 1:3 ratio of the DT-NH peak to the DTE-NH peak indicates that the polymer is made of 25% DT and 75% DTE. The ratio of CH group to the ethyl ester group shows that there are three ethyl ester groups for every four monomer subunits. These spectral data indicate that the polymer contains DT and DTE in 1:3 ratio and the benzyl protecting group is completely removed.

Characterization

The molecular weight of the product was determined by GPC using THF as the mobile phase. A $M_w$ of 115 Kda and $M_n$ 57 Kda were obtained. The $T_g$ of the polymer was found to be 106° C. by DSC and the decomposition temperature (for 10% decomposition) was 309° C.

Example 5

Poly(DT-DTE carbonate) copolymers with DT contents of 20 percent, 40 percent, 60 percent and 100 percent were also prepared. Solvent casting films were made and pH-dependent dissolution and degradation studies were performed. Poly(100% DT carbonate) was found to be stable and insoluble in pH<5 acidic buffer solution. However, 25 to 30 mg polymer film dissolved in 10 mL of PBS of pH7.4 at 37° C. in several hours. Degradation of the dissolved polymer was followed by aqueous GPC using a UV detector at 220 nm. It was observed that the polymer dissolved without significant degradation. When the polymer solution in buffer was incubated at 37° C. the polymer degraded rapidly.

Dissolution and degradation rates of the copolymers decreased with decreasing DT content. The copolymer with 60 percent DT content dissolved in pH 7.4 PBS in one day. The copolymer with 40 percent DT content dissolved in pH 7.4 PBS in two days. The copolymer with 20 percent DT content was not soluble in pH 7.4 PBS at 37° C.

Example 6

Hydrogenolysis of Poly(DTBn-Adipate)

Preparation

In a 500 mL pressure bottle was placed 21 g of poly (DTBn-adipate) having a $M_w$ of 76.8 Kda and $M_n$ of 43.7 Kda. To the bottle was then added 200 mL of DMF and the mixture was stirred until a clear solution was obtained. To this solution were added 4 g of 5% Pd on $BaSO_4$ catalyst. The pressure bottle was attached to the Parr hydrogenator and the air inside the bottle was displaced with hydrogen by alternatively pressurizing with hydrogen and then depressurizing. The bottle was maintained at a hydrogen pressure of 60 psi and then subjected to shaking for 24 h. An aliquot was withdrawn and after suitable treatment examined by $^1H$ NMR which showed complete removal of the benzyl group. The reaction was stopped and the reaction mixture was centrifuged. The supernatant was filtered using a celite bed on a sintered glass funnel. The filtrate was added to 2.0 L of cooled deionized water in a high speed blender. The precipitated product was isolated by filtration and washed with 2.0 L of water. The product was dried in a stream of nitrogen for 16 h and then dried in vacuum oven at room temperature for 2 days.

Structure Proof

The $^1H$ NMR spectrum of the product in DMSO-$d_6$ showed the following resonances (δ, ppm relative to TMS): 8.26 (br s, 0.95H, NH), 7.00–7.09 (m, 8H, aromatic H's), 4.71 (m, 1H, CH of tyrosine), 2.2–3.3 (m, 10H, $CH_2$'s of DAT, Tyrosine and $CH_1$—CO—), 1.74 (t, 4H, $CH_2$—$CH_2$ of adipate). Also, a multiplet that is found in poly(DTBn-adipate) at 5.1 due to benzyl H's was completely absent, indicating complete removal of the benzyl protecting groups. Also, the amide NH peaks had shifted from 8.45 ppm in poly(DTBn-adipate) to 8.26 ppm. The phenyl resonance of the benzyl group at 7.35 ppm was also absent in the product. No other significant changes in the spectrum were observed.

Characterization

The molecular weight of the product was determined by GPC using THF as the mobile phase. A $M_w$ of 36.2 Kda and $M_n$ 25.4 Kda were obtained. The $T_g$ of the polymer was found to be 106° C. by DSC and the decomposition temperature (for 10% decomposition) was 334° C.

Example 7

The Unexpected Acceleration of Polymer Degradation Due to the Presence of Free Carboxylic Acid Groups Poly(DTE carbonate) is a solid, extremely hydrophobic polymer that absorbs less than 3% (by weight) of water and that exhibits no detectable mass loss due to resorption under physiological conditions. Upon incorporation of monomer units with free carboxylic acid groups, these material properties change to an unexpected extent. FIG. 1 illustrates that when x=0.5, f=0, and A=C=O (as defined in Formula VIII), the copolymer will completely resorb (dissolve) within 100 hours at physiological conditions in vitro (phosphate buffered solution, pH 7.4, 37° C.), and when x=0, f=0, and A=C=O (as defined in Formula VIII), the free acid homopolycarbonate will completely resorb (dissolve) within about 7 hours at physiological conditions in vitro.

The polymers with free carboxylic acid groups can be cast into films either by compression molding or by solvent casting and can be fabricated into sponges by salt leaching techniques or by phase separation techniques. The homopolymers (x=0, f=0, and A=C=O as defined in Formula VIII) dissolve in phosphate buffer of pH 7.4 to the extent of 2 mg/mL. When examined by aqueous GPC using UV detection at 200 nm it was found that the polymer dissolved without significant backbone degradation. However, once in solution, backbone degradation to low molecular weight oligomers and eventually to monomer occurred. After 70 h of incubation the peak molecular weight decreased from 40,000 g/mole to about 4,000 g/mole and about 10% of the sample weight consisted of monomer. With poly($DT_{0.5}$-$DTE_{0.5}$ carbonate) the solubility is considerably reduced to 0.2 mg/mL. However, a sample of this polymer also resorbed mostly by dissolution without significant backbone degradation. For copolycarbonates with a DT content of 25 mole percent and lower (x>0.75, f=0, and A=C=O, as defined in Formula VIII), no solubility was observed by HPLC.

The present invention thus provides new free-acid versions of prior art polymers with increased rates of degradation that are prepared by a highly selective palladium-catalyzed hydrogenolysis process. The new polymers satisfy heretofore unmet needs for tissue-compatible implantable biomaterials with reduced, as well as increased, rates of degradation.

The foregoing examples and description of the preferred embodiment should be taken as illustrating, rather than as limiting, the present invention as defined by the claims. As will be readily appreciated, numerous variations and combinations of the features set forth above can be utilized without departing from the present invention as set forth in the claims. Such variations are not regarded as a departure from the spirit and scope of the invention, and all such variations are intended to be included within the scope of the following claims.

What is claimed is:

1. A polymer with a hydrolytically labile polymer backbone, said polymer having the structure:

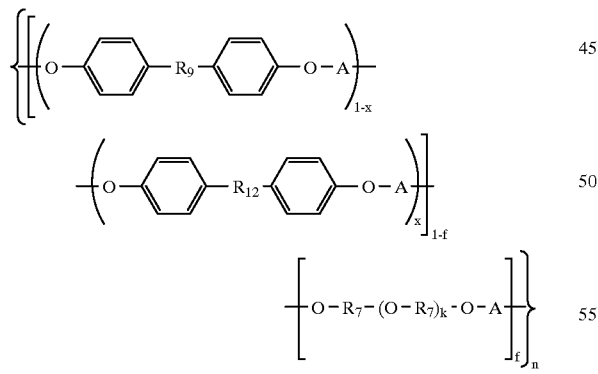

wherein $R_9$ is an alkyl, aryl or alkylaryl group with up to 18 carbon atoms having a pendent carboxylic acid group on the benzyl ester thereof;

$R_{12}$ is an alkyl, aryl or alkylaryl group with up to 18 carbon atoms having a pendent carboxylic acid ester group selected from the group consisting of straight and branched alkyl and alkylaryl esters containing up to 18 carbon atoms and ester derivatives of biologically and pharmaceutically active compounds covalently bonded to said polymer, provided that said ester group is not a benzyl group or a group that is removed by hydrogenolysis;

each $R_7$ is independently an alkylene group containing up to four carbon atoms;

A is selected from the group consisting of:

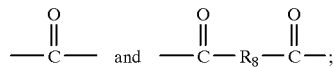

wherein $R_8$ is selected from the group consisting of saturated and unsaturated, substituted and unsubstituted alkyl, aryl and alkylaryl groups containing up to 18 carbon atoms;

k is between about 5 and about 3,000; and x and f independently range from zero to less than one.

2. The polymer of claim 1, wherein x and f are both zero.

3. The polymer of claim 1, wherein $R_9$ has a structure selected from the group consisting of:

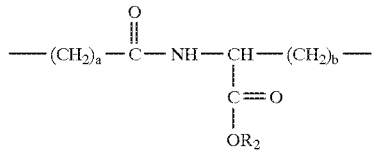

and

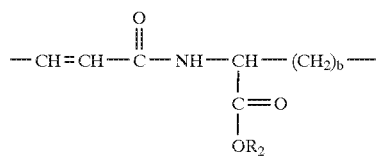

wherein $R_2$ is hydrogen or a benzyl group and a and b are independently zero, one or two.

4. The polymer of claim 3, wherein x is greater than zero and $R_{12}$ has a structure selected from the group consisting of:

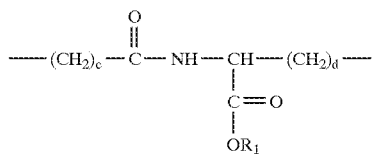

and

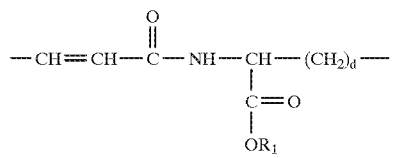

wherein $R_1$ is selected from the group consisting of straight and branched alkyl and alkylaryl groups containing up to 18 carbon atoms and derivatives of biologically and pharmaceutically active compounds covalently bonded to said polycarbonate, provided that $R^1$ is not a benzyl group or a group that is removed by hydrogenolysis; and c and d are independently zero, one or two.

5. The polymer of claim 4, wherein $R_9$ has the structure:

$$-(CH_2)_a-\overset{O}{\underset{\|}{C}}-NH-\underset{\underset{OR_2}{|}}{\underset{C=O}{\underset{|}{CH}}}-(CH_2)_b-$$

and $R_{12}$ has the structure:

$$-(CH_2)_c-\overset{O}{\underset{\|}{C}}-NH-\underset{\underset{OR_1}{|}}{\underset{C=O}{\underset{|}{CH}}}-(CH_2)_d-$$

wherein a and c are two and b and d are one.

6. The polymer of claim 1, wherein x is between about 0.5 and about 0.75.

7. The polymer of claim 1, wherein said ester group of said pendent carboxylic acid ester group of $R_{12}$ is a straight-chained alkyl group selected from the group consisting of ethyl, butyl, hexyl and octyl groups.

8. The polymer of claim 1, wherein said pendent group of $R_9$ is a benzyl carboxylate group.

9. The polymer of claim 1, wherein f is greater than zero.

10. The polymer of claim 9, wherein each $R_7$ group is ethylene.

11. The polymer of claim 9, wherein k is between about 20 and about 200.

12. The polymer of claim 9, wherein f ranges between about 0.05 and about 0.95.

13. An implantable medical device in the form of a sheet consisting essentially of the polymer of claim 9 for use as a barrier for surgical adhesion prevention.

14. A method for preventing the formation of adhesions between injured tissues comprising inserting as a barrier between said injured tissues a sheet consisting essentially of the polymer of claim 9.

15. An implantable medical device comprising the polymer of claim 1.

16. The implantable medical device of claim 15, wherein the surface of said device is coated with said polymer.

17. The implantable medical device of claim 15, comprising a biologically or pharmaceutically active compound in combination with said polymer, wherein said active compound is present in amounts sufficient for therapeutically effective site-specific or systemic drug delivery.

18. The implantable medical device of claim 17, wherein said biologically or pharmaceutically active compound is covalently bonded to said polymer.

19. A method for site-specific or systemic drug delivery comprising implanting in the body of a patient in need thereof an implantable drug delivery device comprising a therapeutically effective amount of a biologically or pharmaceutically active compound in combination with the polymer of claim 1.

20. The method of claim 19, wherein said biologically or pharmaceutically active compound is covalently bonded to said polymer.

21. A controlled drug delivery system comprising a biologically or pharmaceutically active agent physically coated with the polymer of claim 1.

22. A controlled drug delivery system comprising the polymer of claim 1 physically admixed with a biologically or pharmaceutically active agent.

23. A controlled drug delivery system comprising a biologically or pharmaceutically active agent physically embedded or dispersed into a polymeric matrix formed from the polymer of claim 1.

24. A method of regulating cellular attachment, migration and proliferation on a polymeric substrate, comprising contacting living cells, tissues or biological fluids containing living cells with the polymer of claim 1.

25. The method of claim 24, wherein said polymer is in the form of a coating on a medical implant.

26. The method of claim 24, wherein said polymer is in the form of a film.

27. The method of claim 24, wherein said polymer is in the form of a polymeric tissue scaffold.

28. The polymer of claim 1, comprising a polycarbonate in which A is:

$$-\overset{O}{\underset{\|}{C}}-.$$

29. The polymer of claim 1, comprising a polyarylate in which A is:

$$-\overset{O}{\underset{\|}{C}}-R_8-\overset{O}{\underset{\|}{C}}-$$

wherein $R_8$ is selected from the group consisting of saturated and unsaturated, substituted and unsubstituted alkyl groups containing from 2 to 12 carbon atoms.

30. The polyarylate of claim 29, wherein $R_8$ is selected from the group consisting of $-CH_2-C(=O)-$, $-CH_2-CH_2-C(=O)-$, $-CH=CH-$ and $(-CH_2-)_z$, wherein z is an integer between 2 and 8, inclusive.

31. The polyarylate of claim 29, wherein $R_8$ is selected from the group consisting of substituted and unsubstituted aryl and alkylaryl groups containing from 6 to 12 carbon atoms.

32. The polyarylate of claim 31, wherein $R_8$ is a phenyl group.

33. A method for the selective removal of pendent ester side chains comprising the steps of:
   preparing a reaction mixture of the polymer of claim 1, in which the pendent group of $R_9$ is a benzyl carboxylate group, in an anhydrous reaction solvent consisting essentially of one or more solvents selected from the group consisting of N,N-dimethylformamide (DMF), N,N-dimethylacetamide (DMA) and N-methylpyrrolidone (NMP); and
   contacting said reaction mixture with a palladium catalyst in the presence of a hydrogen source, so that the benzyl groups of said pendent benzyl carboxylate groups are selectively removed by hydrogenolysis.

34. The method of claim 33, wherein said hydrogen source comprises hydrogen gas.

35. The method of claim 34, wherein said hydrogen source further comprises 1,4-cyclohexadiene added to said reaction mixture.

36. The method of claim 34, wherein said ester group of said pendent carboxylic acid ester group of $R_{12}$ is a straight-chained alkyl group selected from the group consisting of ethyl, butyl, hexyl and octyl groups.

37. The method of claim 33, wherein said hydrogen source comprises 1,4-cyclohexadiene added to said reaction mixture.

38. The method of claim 37, wherein said 1,4-cyclohexadiene is added to said reaction mixture before said reaction mixture is contacted with said palladium catalyst.

39. The method of claim 33, wherein said palladium catalyst comprises palladium on barium sulfate.

40. The method of claim 33, wherein A is:

so that said polymer is a polycarbonate.

41. The method of claim 40, wherein f is greater than zero.

42. The method of claim 33, wherein A is:

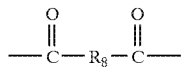

so that said polymer is a polyarylate.

43. The method of claim 42, wherein f is greater than zero.

44. The method of claim 33, wherein x is zero.

45. The method of claim 33, wherein $R_9$ has a structure selected from the group consisting of

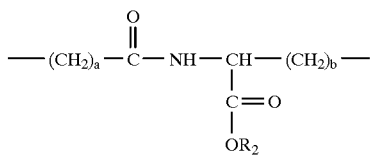

and

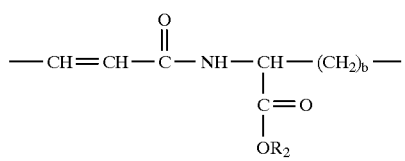

wherein $R_2$ is a benzyl group and a and b are independently zero, one or two.

46. The method of claim 45, wherein $R_9$ has the structure:

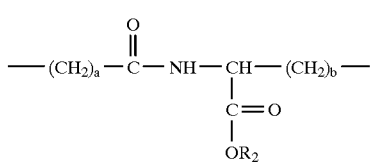

wherein a is two and b is one.

47. The method of claim 45, wherein $R_{12}$ has a structure selected from the group consisting of:

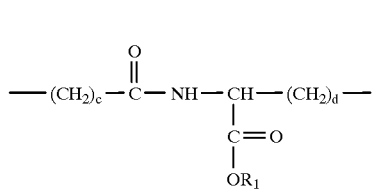

and

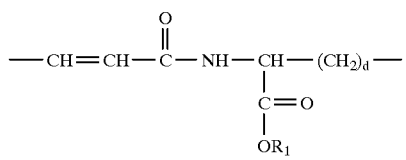

wherein $R_1$ is selected from the group consisting of straight and branched alkyl and alkylaryl groups containing up to 18 carbon atoms and derivatives of biologically and pharmaceutically active compounds covalently bonded to said polymer, with the proviso that $R_1$ is not a benzyl group or a group that is removed by hydrogenolysis, and c and d are independently zero, one or two.

48. The method of claim 46, wherein $R_{12}$ has the structure:

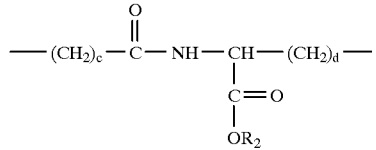

wherein c is two and d is one.

49. The method of claim 48, wherein a and c are two and b and d are one.

50. The method of claim 33, wherein x is between about 0.50 and 0.75.

UNITED STATES PATENT AND TRADEMARK OFFICE
CERTIFICATE OF CORRECTION

PATENT NO.     : 6,120,491
DATED          : September 19, 2000
INVENTOR(S)    : Kohn et al.

It is certified that error appears in the above-identified patent and that said Letters Patent is hereby corrected as shown below:

Column 1,
Line 13, "now U.S. Pat. No. 5,293,682" should be deleted.

Signed and Sealed this

Third Day of December, 2002

JAMES E. ROGAN
*Director of the United States Patent and Trademark Office*